(12) United States Patent
Saitou

(10) Patent No.: US 8,652,055 B2
(45) Date of Patent: Feb. 18, 2014

(54) ELECTRONIC HEMOMANOMETER, METHOD OF CORRECTING PULSE WAVE DATA OF ELECTRONIC HEMOMANOMETER, PROGRAM FOR CAUSING A COMPUTER TO EXECUTE PROCEDURES AND COMPUTER-READABLE RECORDING MEDIUM

(75) Inventor: Yukiyoshi Saitou, Machida (JP)

(73) Assignee: Shisei Datum Co., Ltd., Tokyo (JP)

( * ) Notice: Subject to any disclaimer, the term of this patent is extended or adjusted under 35 U.S.C. 154(b) by 107 days.

(21) Appl. No.: 13/152,167

(22) Filed: Jun. 2, 2011

(65) Prior Publication Data

US 2011/0237964 A1 Sep. 29, 2011

Related U.S. Application Data

(62) Division of application No. 11/659,859, filed as application No. PCT/JP2005/014874 on Aug. 9, 2005, now abandoned.

(30) Foreign Application Priority Data

Aug. 12, 2004 (JP) ................................. 2004-235267

(51) Int. Cl.
*A61B 5/02* (2006.01)

(52) U.S. Cl.
USPC .......................................... 600/494; 600/490

(58) Field of Classification Search
USPC ........................................ 600/494, 500–502
See application file for complete search history.

(56) References Cited

U.S. PATENT DOCUMENTS

| 4,638,810 | A | | 1/1987 | Ramsey, III et al. |
| 5,014,714 | A | | 5/1991 | Millay et al. |
| 5,054,494 | A | * | 10/1991 | Lazzaro et al. ............... 600/490 |
| 5,699,807 | A | | 12/1997 | Motogi et al. |
| 6,036,653 | A | | 3/2000 | Baba et al. |
| 6,893,403 | B2 | * | 5/2005 | Kolluri et al. ................. 600/494 |
| 7,198,604 | B2 | * | 4/2007 | Kolluri et al. ................. 600/490 |
| 2005/0119578 | A1 | | 6/2005 | Kubo |

FOREIGN PATENT DOCUMENTS

| JP | S63-286135 A | 11/1988 |
| JP | H5-317274 A | 12/1993 |
| JP | H8-89485 A | 4/1996 |

* cited by examiner

*Primary Examiner* — Navin Natnithithadha
*Assistant Examiner* — Michael R Bloch
(74) *Attorney, Agent, or Firm* — DLA Piper LLP (US)

(57) ABSTRACT

A pulse wave data correcting method in an electronic hemomanometer which is designed to time-differentiate signals each formed by superposing a pulse wave amplitude component on a cuff pressure, to compute an envelope consisting of the time-differentiated signals, to detect the maximal value in the computed envelope, to sort the time-differentiated signals generated prior to the maximal envelope value in ascending order, to sort the time-differentiated signals generated after the maximal envelope value in descending order, and to form an envelope consisting of the sorted time-differentiated signals.

6 Claims, 5 Drawing Sheets

PRIOR ART

US 8,652,055 B2

ELECTRONIC HEMOMANOMETER, METHOD OF CORRECTING PULSE WAVE DATA OF ELECTRONIC HEMOMANOMETER, PROGRAM FOR CAUSING A COMPUTER TO EXECUTE PROCEDURES AND COMPUTER-READABLE RECORDING MEDIUM

This is a Divisional Application under 37 CFR §1.53(b) of application Ser. No. 11/659,859 of Feb. 9, 2007 filed based on PCT/JP2005/014874 of Aug. 9, 2005, which is hereby incorporated in its entirety by reference.

FIELD OF THE INVENTION

The present invention relates to an electronic hemomanometer and a hemodynamic measurement type hemomanometer.

BACKGROUND ART

In the past, a pulse wave pattern has been smoothed by smoothing the amplitude values of pulse waves with moving average. For example, see Japanese Patent Application Laid-Open (Kokai) No. Hei 5-317274.

In other words, the prior art has simply moving-averaged and smoothened time-series data of output data F (Pn) corresponding to discrete input data Pn in time series.

FIG. 4 is a characteristic curve exemplifying a relationship between differential pressures across a blood vessel wall and changes in the blood vessel volume.

It is found from such a characteristic curve that the blood volume sharply increases at a position in which the internal pressure of the blood vessel exceeds the external pressure (cuff pressure) (i.e., a sharply changing point as shown in FIG. 4). The rapid change in the volume of the blood vessel is due to the fact that the media of the blood vessel is rich in extensibility. As the differential pressure across the blood vessel wall increases, the volume of the blood vessel will not change very much. This is due to the fact that the change of the blood vessel volume is limited by the fibrous adventitia of the blood vessel.

FIG. 5 is a curve showing a relationship between the differential pressures across the blood vessel wall and the differentiated values of change in the blood vessel volume.

The prior art could not directly measure the volume of a blood vessel for measuring a blood pressure. Therefore, the prior art used a method of measuring a blood pressure value based on discrete volume changes generated by heartbeat (i.e., a pulse wave pattern) (oscillometric method).

FIG. 6 shows an actual pulse wave pattern.

The actual pulse wave (which is shown by solid line) is an uneven pattern in comparison with an ideal pattern as shown by dotted line. The uneven pattern prepared based on the actual measurements is due to the fact that the blood pressure itself fluctuates in terms of time and also due to the fact that the cuff pressure changes on movement of human's body or other factor.

Patent Publication 1 Japanese Patent Application Laid-Open (Kokai) No. Hei 5-317274.

SUMMARY OF THE INVENTION

FIG. 7 is an erroneous judgment of blood pressures in the prior art.

If the adjacent pulse wave amplitudes greatly fluctuate to cause a pattern or graph of the amplitude to be deformed, a problem has raised in that the judgment of the maximal blood pressure itself was disturbed as shown in FIG. 7.

When the maximal blood pressure is to be judged in the oscillometric method, it is judged that the fixed rate of the peak (maximum) value of the pulse wave amplitude (which is 30% in FIG. 7) corresponds to the maximal blood pressure.

In such a case of FIG. 7 wherein the peak values are 30% at points A, B and C, if it is judged that the maximal blood pressure is at the point C in spite of the true value of the maximal blood pressure at the point A, this will lead to an erroneous judgment that the judged maximal blood pressure is lower than the true value.

In order to avoid such an erroneous judgment, it may be considered that, for example, it is judged that a blood pressure sensed when it first exceeds a value to be judged (30%) is the maximal blood pressure as the volume of blood vessel gradually increases. In such a case, however, another problem is raised in that if a larger pulse wave peak exceeding 30% appears leftward of the point A in FIG. 7, it will be erroneously judged to be the maximal blood pressure.

Also when the minimal blood pressure is to be judged, the same problem will be raised.

In the prior art, an amount to be corrected was determined only by the relationship between the adjacent numeral values regardless of the characteristic which should be provided inherently. Therefore, a plurality of peaks may remain after being processed, as shown in FIG. 7. In order to prevent the occurrence of these plural peaks, a pattern may be smoothed enough by increasing the number of data points in moving average.

However, still another problem may be raised in that the inherently correct information is lost if the number of data points in the moving average is increased too much. In addition, the error in correction will be increased by a simple condition of correction between data.

An object of the present invention is to provide a pulse wave data compensator of electronic hemomanometer, a method of controlling an electronic hemomanometer, an electronic hemomanometer, a method of correcting pulse wave data in an electronic hemomanometer, a program and a recording medium, all of which can easily and reliably correct erroneous measurements in a pulse wave pattern.

The present invention observes output data F (Pn) corresponding to discrete input data Pn in time series, and uses the monotonic increase or decrease of the observed output data F (Pn) to correct them so that the values of the output data F (Pn) will be interchanged with one another in a direction of time axis.

In accordance with the present invention, the erroneous measurements in the pulse wave pattern are corrected using a simple algorithm in which the values are sequentially interchanged with one another. Thus, the measurement errors in the pulse wave pattern can be corrected in an easy and sure manner.

BEST MODE FOR CARRYING OUT THE INVENTION

First Embodiment

Figure 1:
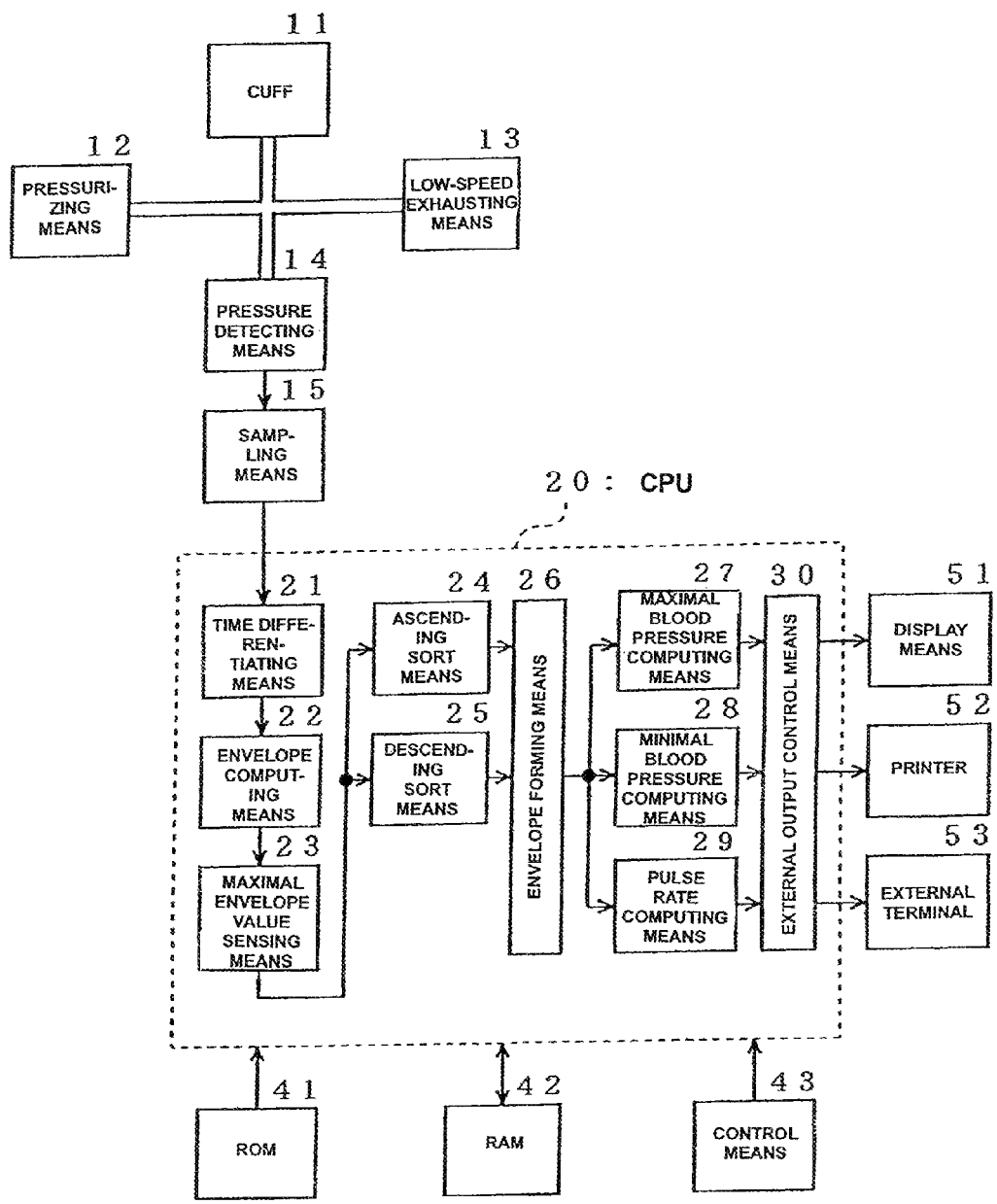
FIG. 1 is a block diagram showing an electronic hemomanometer 100 according to the first embodiment of the present invention.

FIG. 1 is a block diagram showing an electronic hemomanometer 100 according to the first embodiment of the present invention.

The electronic hemomanometer 100 comprises a cuff 11, a pressurizing means 12, a low-speed evacuating means 13, a pressure sensing means 14, a sampling means 15, a CPU 20, a ROM 41, a RAM 42, an operative means 43, a display means 51, a printer 52 and an external terminal 53.

The cuff 11 can be wound around an arm of a person to be measured. The pressurizing means 12 is to pressurize the cuff 11 to a pressure necessary to measure a blood pressure. The low-speed evacuating means 13 is to gradually evacuate the cuff 11 which had been pressurized by the pressurizing means 12.

The pressure sensing means 14 includes a pressure transducer for sensing the pressure in the cuff 11 and converting the sensed pressure into an electrical signal (pulse) which is in turn outputted therefrom.

The sampling means 15 counts the electrical signals (pulses) outputted from the pressure sensing means 14 within a predetermined time period. The counting is periodically repeated based on a sampling signal. The sampling means 15 then analog to digital (A/D) converts the sampled value.

The cuff 11, pressurizing means 12, low-speed evacuating means 13 and pressure sensing means 14 are mutually connected through flexible pipes.

The CPU 20 controls the entire electronic hemomanometer 100 and functionally cooperates with a program stored in the ROM 41 to realize a time differentiating means 21, an envelope computing means 22, a maximal envelope value detecting means 23, an ascending sort means 24, a descending sort means 25, an envelope forming means 26, a maximal blood pressure computing means 27, a minimal blood pressure computing means 28, a pulse rate computing means 29 and an external output control means 30.

The ROM 41 is a memory which has stored a program as shown by a flow chart of FIG. 2 which will be described later. The RAM 42 is a memory for storing the computed results of the CPU 20 and others. The operative means 43 includes conventional function keys and others.

The pressurizing means 12, low-speed evacuating means 13, pressure sensing means 14 and sampling means 15 are controlled by the CPU 20.

The time differentiating means 21 time-differentiates signals each formed by superposing a pulse wave amplitude component on a cuff pressure to generate time-differentiated signals (S8).

Where the cuff pressures are taken on one axis of the X-Y coordinate while the time-differentiated signals from the time differentiating means 21 are taken on the other axis of the X-Y coordinate, the envelope computing means 22 plots the maximal values of the time-differentiated signals for every heartbeat and computes an envelope formed by connecting the plotted maximal values (S9).

The maximum envelope detecting means 23 detects the maximal value in the computed envelope (S10).

The ascending sort means 24 sorts the time-differentiated signals generated prior to the maximal envelope value in ascending order (S11).

The descending sort means 25 sorts the time-differentiated signals generated after the maximal envelope value in descending order (S12).

The envelope forming means 26 forms envelopes consisting of the time-differentiated signals sorted by the ascending and descending sort means (S 13).

The maximal blood pressure computing means 27 is to compute the maximal blood pressure based on the formed envelopes of time-differentiated signals (S14).

The minimal blood pressure computing means 28 computes the minimal blood pressure based on the formed envelope of time-differentiated signals (S14).

The pulse rate computing means 29 is to compute a pulse rate based on the time interval between the peaks in the formed envelopes of time-differentiated signals (S15).

The external output control means 30 causes the CPU 20 to externally output the maximal blood pressure computed by the maximal blood pressure computing means 27, the minimal blood pressure computed by the minimal blood pressure computing means 28 and the pulse rate computed by the pulse rate computing means 29 (S16).

The display unit 51 is a device for visually displaying the computed maximal blood pressure, minimal blood pressure and pulse rate. The printer 52 is a device for printing the computed maximal blood pressure, minimal blood pressure and pulse rate.

The operation of the first embodiment of the present invention will now be described.

Figure 2:
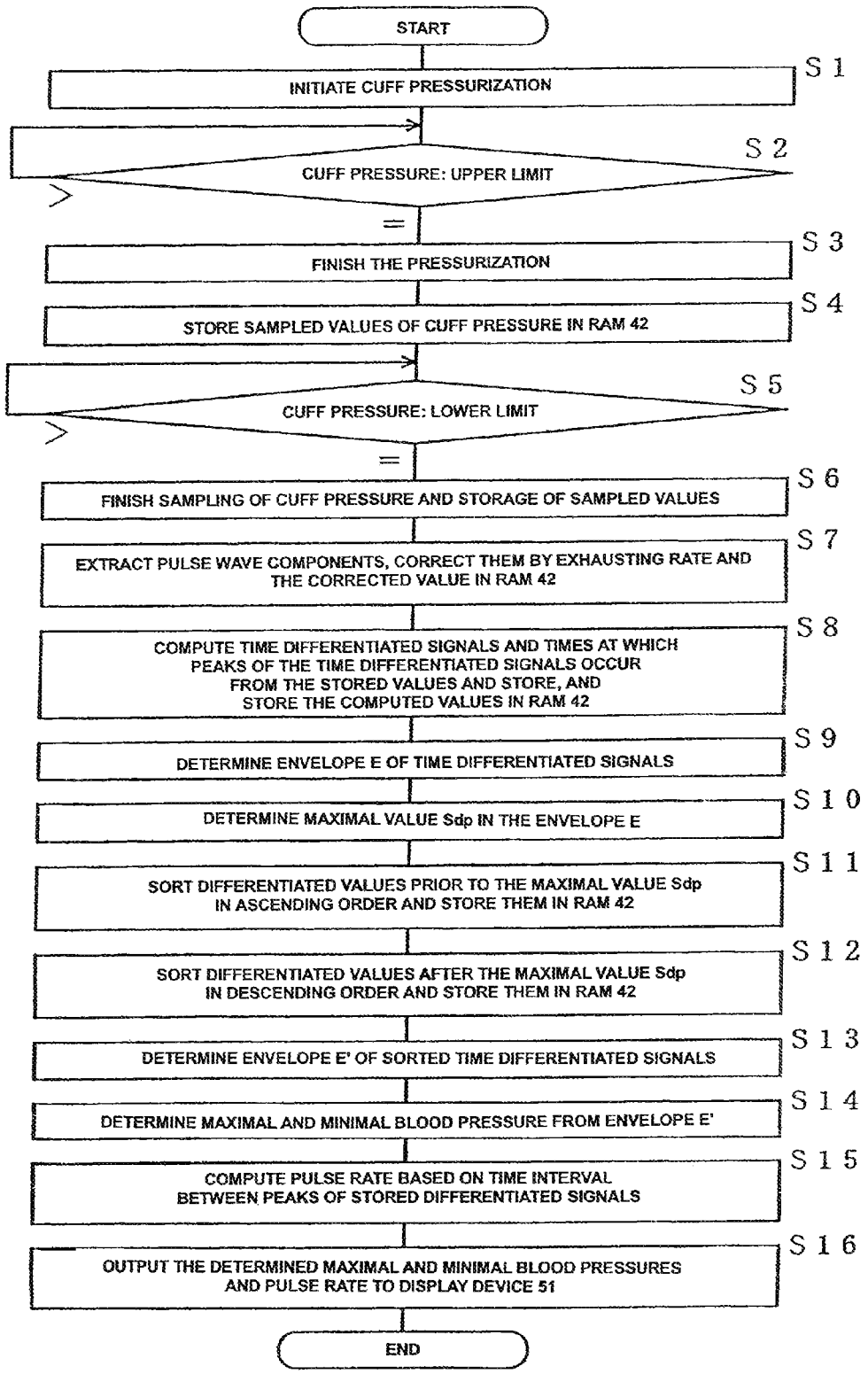
FIG. 2 is a flow chart showing the operation of the first embodiment of the present invention.

FIG. 2 is a flow chart illustrating the operation of the first embodiment of the present invention.

The cuff is first pressurized (S1). If the cuff pressure has been equal to the upper limit (S2), the pressurization is stopped (S3). The sampled values of cuff pressure are stored in the RAM 42 (S4). If the cuff pressure has been lower than the lower limit (S5), the sampling of the cuff pressure and the storing of the sampled values are finished (S6).

Thereafter, pulse wave components are extracted and corrected by the exhaust rate. Their values are stored in the RAM 42 (S7). The discrete values of change in the blood vessel volume (pulse wave amplitudes) to be provided monotonously increase if the blood pressure does not fluctuate during the measurement. After the pulse wave amplitudes have passed the peak, they monotonously decrease.

Figure 6:
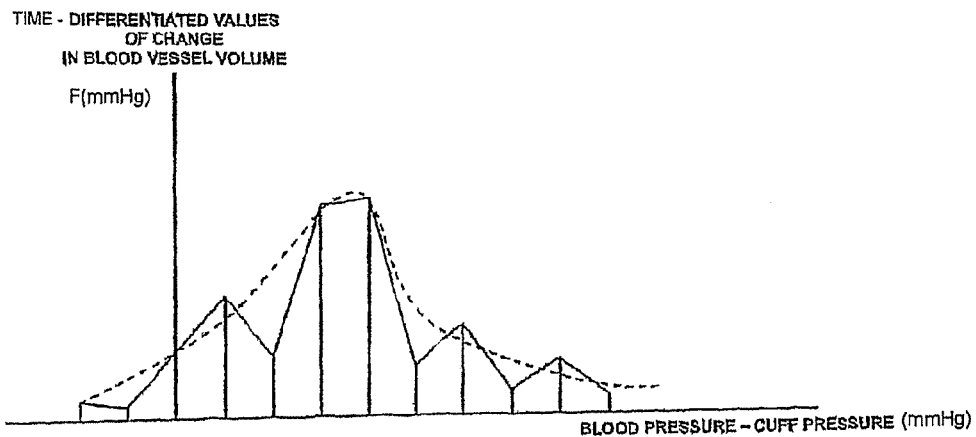
FIG. 6 is a graph showing an actual pulse wave pattern.
Figure 7:
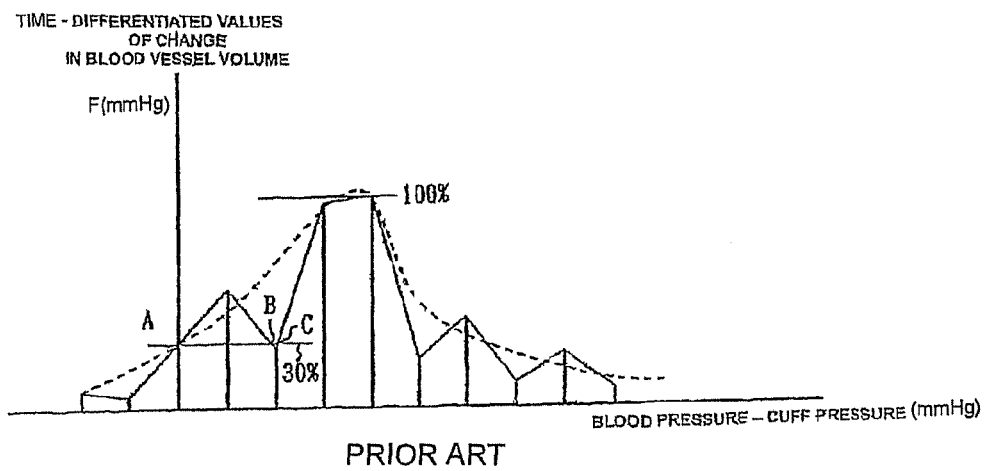
FIG. 7 is a graph showing erroneous measurements of blood pressure according to the prior art.

As shown in FIG. 6, the occurrence of irregularity is due to the fact that the values along the X axis in FIG. 6 (or blood pressure-cuff pressure) differ from true values depending on changes in blood pressure, movement of human's body and other factors. Thus, it may be considered that, if the obtained pulse wave pattern is to be corrected, the fluctuation of output value in the Y axis occurs depending on the change of input value along the X axis.

Figure 3:
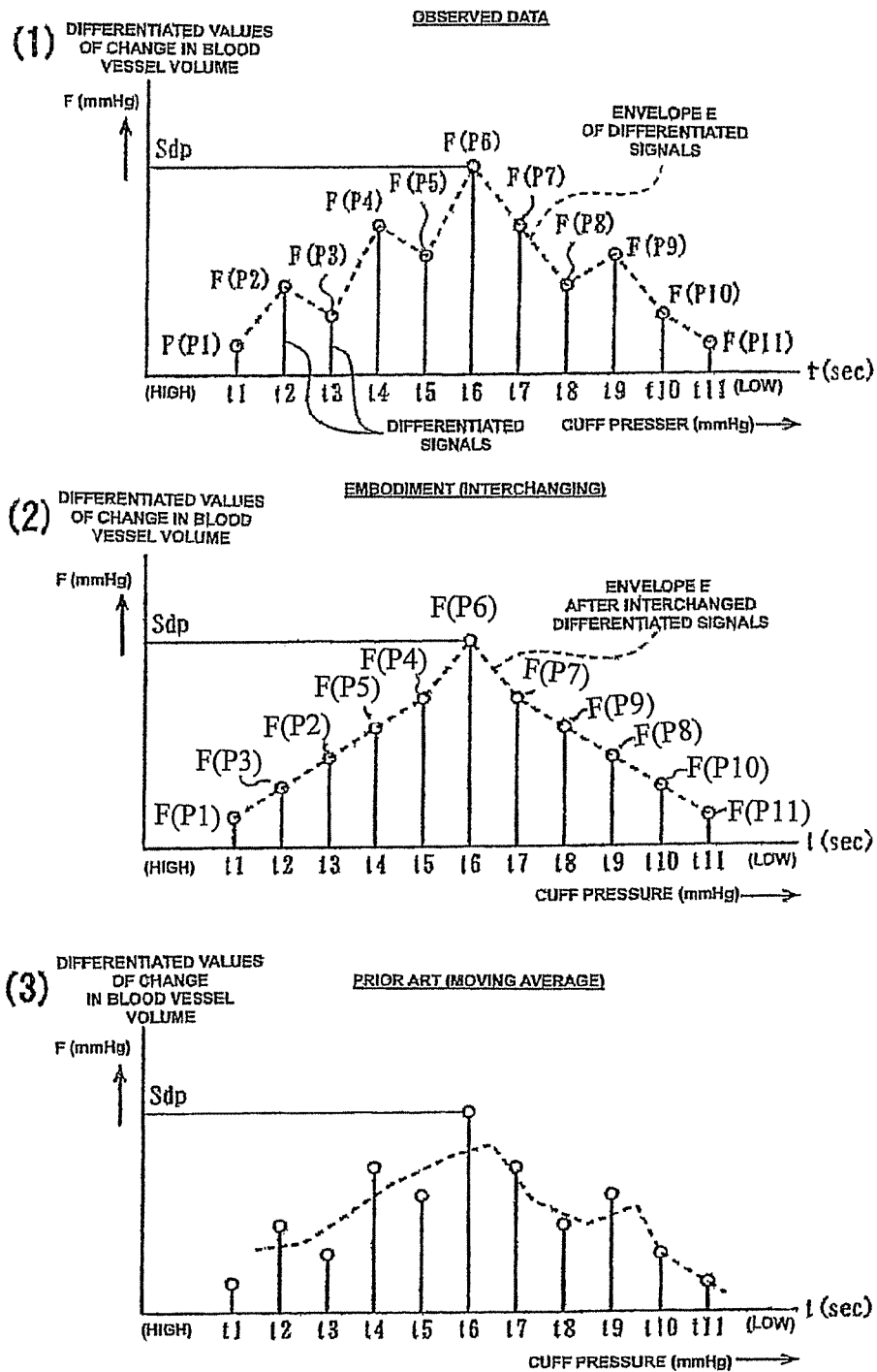
FIG. 3 is a graph showing a relationship between cuff pressures and differentiated values of change in a blood vessel volume (observed data)
Figure 4:
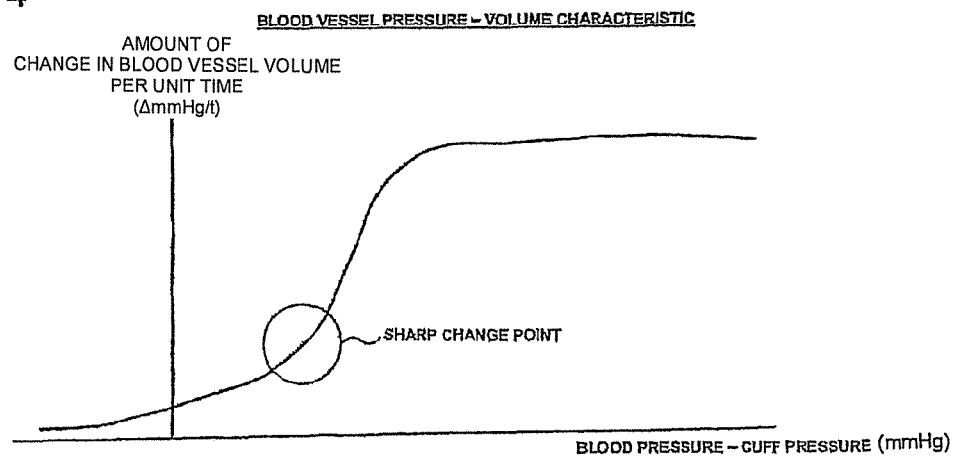
FIG. 4 is a characteristic graph showing a relationship between differential pressures across a blood vessel wall and blood vessel volumes.
Figure 5:
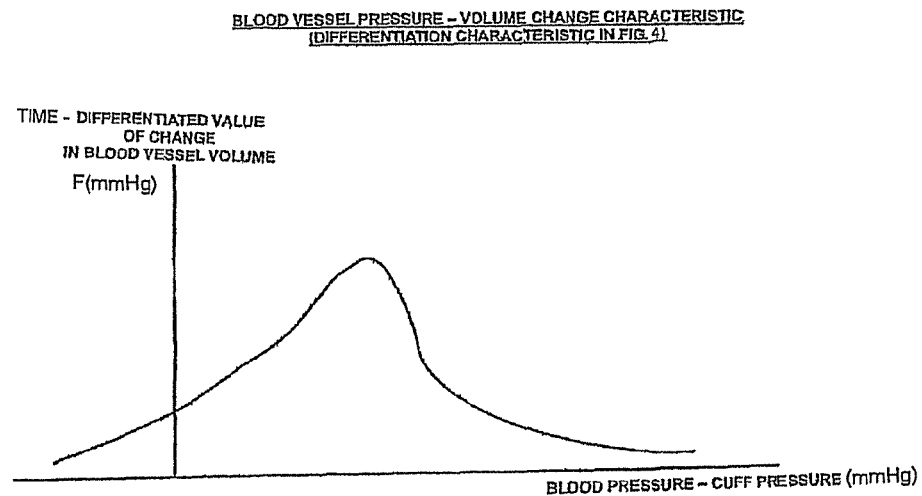
FIG. 5 is a graph showing a relationship between the differential pressures across the blood vessel wall of FIG. 4 and the differentiated values of change in the blood vessel volume.

FIG. 3 is is composed of three graphs showing a relationship between cuff pressures and differentiated values of change in a blood vessel volume (observed data) as follows:

FIG. 3(1) shows observed data, the broken line showing an envelope E connecting the peak values in the differentiated signals.

In FIG. 3(2), the broken line shows an envelope E' after the differentiated signals have been sorted in the first embodiment of the present invention.

In FIG. 3(3), the broken line shows an envelope of differentiated signals formed from the results of observed data in FIG. 3(1) after they have been subjected to moving average in the prior art. FIG. 3(3) shows that a plurality of peaks remain. One peak is between times t6 and t7 while another peak is between times T9 and T10.

In such a manner, the pulse wave pattern can be corrected by dividing the data into right- and left-hand data about the maximal peak value (at time t6 shown in FIG. 3(1)), the right- and left-hand data being then sorted in ascending and descending orders, respectively. In other words, in FIG. 3(1), the data on the left side of the maximal peak at time t6 are sorted in ascending order while the data on the right side of the time t6 are sorted in descending order. The sorted data are then converted into input pressures (blood pressure-cuff pressure). Such a correction gives such a graph as shown in FIG. 3(2).

Thus, the pulse wave pattern so obtained will have a single hump characteristic which regularly has a single peak value as shown in FIG. 3(2).

The first embodiment of the present invention enables the correction of waveform to be realized by executing a simple logic (or sorting in ascending and descending orders).

The first embodiment of the present invention can also estimate noises in a measuring system or arrhythmia after the data have been sorted. More particularly, the observed data shown in the FIG. 3 (1) require that the differentiated values of change in the blood vessel volume at times t2 and t3 are replaced by each other, that the differentiated values of change in the blood vessel volume at times t4 and t5 are replaced by each other and that the differentiated values of change in the blood vessel volume at times t8 and t9 are replaced by each other. it is thus considered that the changes of blood vessel volume fluctuate as much. This enables concrete numerical values to be estimated relating to noises generated by movement of human's body or fluctuations of heartbeat and other factors. In other words, it can be said that, as "the differentiated values of change in the blood vessel volume" are more interchanged from one to another and as the movement in FIG. 3(1) increases, the fluctuation in heartbeat more increases. Hereby, one can precisely evaluate the reliability of the measuring system used, the frequency of the arrhythmia and so on.

If an approximation is executed through moving average or exponential function after the data have been sorted and corrected, one can compute a more accurate and stable pulse wave pattern.

According to the first embodiment of the present invention, the blood pressure in an exercising person can be accurately measured since the fluctuation thereof during measurement can be absorbed.

Further, the first embodiment of the present invention can easily and assuredly correct the measurement error in the pulse wave pattern by performing a simple sorting or weighting step.

Still further, the first embodiment of the present invention can correct the measured values in the pulse wave pattern regardless of cause of noise components.

In addition, the first embodiment of the present invention can mathematically verify the measurement accuracy by defining the probability density function relating to the noise. In other words, the accuracy of the blood pressure measurement should be able to be analogized based on the frequency and magnitude of sorting since the accuracy of the blood pressure measurement by the oscillometric method is deteriorated by fluctuation in the heartbeat.

By the way, if there are a plurality of maximal values in the computed envelope in the above-mentioned embodiment, a true maximal value Sdp will be determined by any one of the following techniques:

(1) A technique that determines any one of the maximal values as a true maximal value according to a predetermined criteria;

(2) a technique that compares each of the maximal values with the adjacent data thereof and considers one maximal value having the largest difference as a noise, the one maximal value being then deleted; and (3) A technique that determines the maximal value at the central portion of the envelope as a true maximal value.

Furthermore, the first embodiment of the present invention can precisely measure the blood pressure regardless of arrhythmia.

In other words, the above-mentioned embodiment of the present invention provides a pulse wave data corrector for electronic hemomanometer, which comprises an output data observing means for observing output data F (Pn) corresponding to discrete input data Pn in time series, and a correction means for correcting the output data F (Pn) using monotonic increase or decrease of the output data F (Pn).

The above-mentioned embodiment of the present invention also provides an electronic hemomanometer which comprises a time differentiating means for time-differentiates signals each formed by superposing a pulse wave amplitude component on a cuff pressure to time-differentiated signals; an envelope computing means for computing an envelope of the time-differentiated signals; a maximal envelope value detecting means for detecting the maximal value in the computed envelope; an ascending sort means for sorting the time-differentiated signals generated prior to the maximal envelope value in ascending order; a descending sort means for sorting the time-differentiated signals generated after the maximal envelope value in descending order; and an envelope forming means for forming an envelope consisting of the time-differentiated signals sorted by the ascending and descending sort means.

In addition, the above-mentioned embodiment of the present invention can be grasped as a program. In other words, the above-mentioned embodiment of the present invention can provide a program for causing a computer to execute an output data observation procedure for observing output data F (Pn) corresponding to discrete input data Pn in time series and for storing the observed data in a memory, and a correction procedure for correcting the value of output data F (Pn) using monotonic increase or decrease of the output data F (Pn) and for storing the corrected values in the memory.

Another program according to the above-mentioned embodiment of the present invention causes a computer to execute a time differentiating procedure for time-differentiates signals each formed by superposing a pulse wave amplitude component on a cuff pressure to obtain time-differentiated signals and for storing them in a memory; an envelope computing procedure for computing an envelope consisting of the time-differentiated signals and for storing it in the memory; a maximal envelope value detecting procedure for detecting the maximal value in the computed envelope and for storing it in the memory; an ascending sort procedure for sorting the time-differentiated signals generated prior to the maximal envelope value in ascending order and for storing them in the memory; a descending sort procedure for sorting the time-differentiated signals generated after the maximal envelope value in descending order and for storing them in the memory; and an envelope forming procedure for forming an envelope consisting of the time-differentiated signals sorted by the ascending and descending sorting procedures and for storing it in the memory.

The aforementioned programs may be stored in a recording medium such FD, CD, DVD, semiconductor memory or the like.

The invention claimed is:

1. An electronic hemomanometer comprising:
    a pressure sensing means for detecting cuff pressure;
    a central processing unit configured to:
    generate time-differentiated signal by superposing a pulse wave amplitude component on the cuff pressure;
    compute an envelope consisting of the time-differentiated signals;
    detect a maximal value in the computed envelope;
    interchange time-differentiated signals in the computed envelope before the maximal envelope value to form an ascending portion and after the maximal envelope value to form a descending portion;
    form the envelope based upon the time differentiated signals sorted in ascending and descending order;
    compute maximal and minimal blood pressures based on the formed envelope.

2. The electronic hemomanometer as claimed in claim 1,
    further comprising a display in communication with the central processing unit,
    wherein the central processing unit is configured to display the computed maximal and minimal blood pressures on the display.

3. The electronic hemomanometer as claimed in claim 1, wherein the central processing unit is further configured to compute a pulse rate based on time intervals between peaks in the formed envelope.

4. The electronic hemomanometer as claimed in claim 3,
    further comprising a display in communication with the central processing unit,
    wherein the central processing unit is configured to display the pulse rate on the display.

5. A method of correcting pulse wave data in an electronic hemomanometer, comprising:
    a time differentiating step of time-differentiating signals each formed by superimposing a pulse wave amplitude component on a cuff pressure to obtain-differentiated signals and of storing obtained results in a tangible memory of the hemomanometer;
    an envelope computing step of computing an envelope consisting of the time-differentiated signals and of storing computed results in the memory;
    a maximal envelope value detecting step of detecting a maximal value in the computed envelope and of storing detected results in the memory;
    a sorting step of sorting the time-differentiated signals into an ascending and descending portions around the maximal envelope value while conserving all time-differentiated signals on each side of the maximal envelope value, and storing sorted results in the memory;
    an envelope forming step of forming an envelope consisting of the time differentiated signals sorted in the ascending and descending sort steps and of storing the formed envelope in the memory; and
    computing maximal and minimal blood pressures based on the formed envelope.

6. A tangible non-transitory computer readable recording medium stored with a program for causing a computer in a hemomanometer to execute:
    a time differentiating procedure for time-differentiating signals each formed by superimposing a pulse wave amplitude component on a cuff pressure to obtain time-differentiated signals and for storing obtained results in a tangible memory of said hemomanometer;
    an envelope computing procedure for computing an envelope consisting of the time-differentiated signals and for storing computed results in memory;
    a maximal envelope value detecting procedure for detecting the maximal value in the computed envelope and for storing detected results in the memory;
    an interchanging procedure for interchanging time-differentiated signals in the computed envelope before the maximal envelope value to form an ascending portion and after the maximal envelope to form a descending portion, and for storing sorted results in the memory;
    an envelope forming procedure for forming an envelope consisting of the time-differentiated signals sorted by the ascending and descending sorting procedures and for storing the formed envelope in the memory; and
    a computing procedure for computing maximal and minimal blood pressures based on the formed envelope.

* * * * *